United States Patent [19]

Sakai et al.

[11] Patent Number: 5,807,394

[45] Date of Patent: Sep. 15, 1998

[54] SURGICAL INSTRUMENT

[75] Inventors: Junya Sakai, Inuyama; Heiji Yoshinaka; Masaru Ohyama, both of Kagoshima; Kenji Sumiya, Ichikawa; Takashi Nemoto, Nagareyama, all of Japan

[73] Assignee: Mizuho Ika Kogyo Kabushiki Kaisha, Tokyo-To, Japan

[21] Appl. No.: 592,059

[22] Filed: Jan. 26, 1996

[30] Foreign Application Priority Data

Jan. 31, 1995 [JP] Japan .................................... 7-014357

[51] Int. Cl.⁶ ..................................................... A61B 17/00
[52] U.S. Cl. ............................................... 606/39; 606/167
[58] Field of Search ................................ 606/1, 166, 167, 606/170, 27, 37–40, 46–52; 423/445

[56] References Cited

U.S. PATENT DOCUMENTS

| 4,198,382 | 4/1980 | Matsui | 423/445 |
|---|---|---|---|
| 4,225,569 | 9/1980 | Matsui et al. | 423/445 |
| 5,053,035 | 10/1991 | McLaren . | |
| 5,222,987 | 6/1993 | Jones . | |
| 5,258,002 | 11/1993 | Jeffers et al. | 606/167 |

*Primary Examiner*—William Lewis
*Attorney, Agent, or Firm*—Ladas & Parry

[57] ABSTRACT

To ensure continuous incising or coagulating technique without adhesion of carbonized body tissue proteins and fats which may be produced by thermal action of an arc discharge or Joule heat attendant on the electrotomy or electrocoagulation, at least a part of a surgical instrument, such as an electric knife or a forceps, is formed of a C/C composite material.

18 Claims, 1 Drawing Sheet

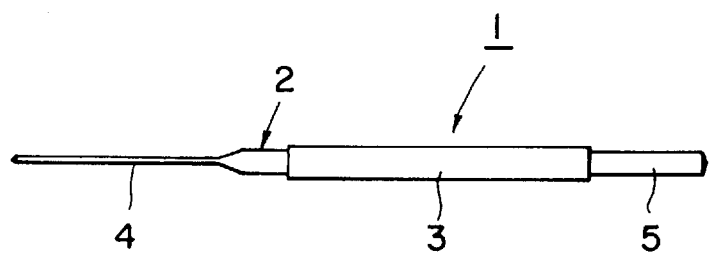
F I G. 1
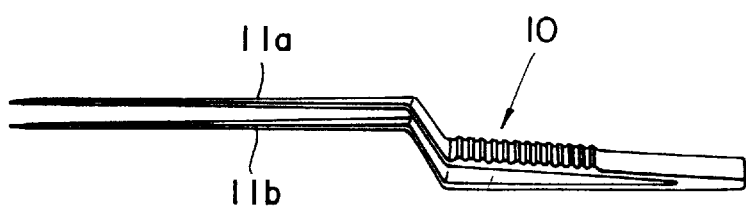
F I G. 2

SURGICAL INSTRUMENT

BACKGROUND OF THE INVENTION

1. Field of the Invention

The present invention relates, to a surgical instrument, such as an electric knife, for use in living body tissue electrotomy or electrocoagulation.

2. Description of the Related Art

A surgical instrument such as an electric knife is a versatile operating appliance capable of living body tissue incisions (electrotomy) and coagulation (electrocoagulation) by passing a high-frequency current from its tip electrode through the body tissue. The tip electrode of such an electric knife is typically made of a stainless steel (JIS (Japanese Industrial Standards), SUS 304 (stainless steel: $Cr_{18}Ni_8Fe$)) because of its resistance to heat, electrical conductivity, and corrosion resistance.

During the execution of the tissue electrotomy or electrocoagulation by use of the electric knife, a high-frequency discharge occurs between the tip electrode and the living body tissue accompanied by a hopping phenomenon peculiar to the high-frequency current. At that time, the stainless steel tip electrode is subjected to adhesion thereto of body tissue proteins and fats carbonized by the thermal action of the arc discharge and the Joule heat attendant on the electrotomy or the electrocoagulation, which would prevent the incising or coagulating technique from being consecutively performed, resulting in an impediment to a successful operation.

A sandpaper-like knife tip cleaner is well known as a measure to remove carbides adhered to the tip electrode of the electric knife. Use of the knife tip cleaner for the removal of carbides adhered to the tip electrode may however cause deformation of the edge of the knife due to abrasion of the metallic material forming the tip electrode by the abrasive action of the knife tip cleaner, or adhesion arising from abraded metallic powder.

For this reason, another type of electric knife has been developed whose stainless steel tip electrode surface is coated with Teflon (PTFE) (Tradename of E. I. du Pont de Nemours & Co. Inc.). This type of knife has an advantage over the bare stainless steel tip electrode in that adhesion of carbides onto the tip electrode is significantly reduced, but this type of knife is disadvantageous in service durability because the Teflon coating on the surface of the tip electrode is caused to dissociate and evaporate therefrom due to the occurrence of a spark discharge of the high-frequency current, with the result that using the Teflon-coated tip electrode only several times would render it equivalent to the bare stainless steel tip electrode.

As a knife tip material having a less tendency for the carbides to adhere to the surface compared with the stainless steel, a silver-copper alloy with a lower specific resistance than that of the stainless steel has been selected and used to fabricate a knife tip electrode for practical use. This attempt was however unsuccessful in completely avoiding the adhesion of carbides on the tip electrode although the adhesion was reduced to a certain extent as compared with the case of the stainless steel tip electrode.

SUMMARY OF THE INVENTION

The present invention was conceived in view of the above problems. It is therefore the object of the invention to provide a surgical instrument free from adhesion of carbides of proteins and fats of living body tissues which may be generated by the thermal action of an arc discharge or Joule heat attendant on the electrocoagulation or electrotomy, thereby enabling continuous incision or coagulation technique to be performed.

According to an aspect of the present invention, there is provided a surgical instrument comprising at least a part formed of a carbon/carbon composite material.

According to another aspect of the present invention, there is provided an electric knife comprising a blade portion formed of a carbon/carbon composite material.

According to a further aspect of the present invention, there is provided a forceps comprising a blade portion formed of a carbon/carbon composite material.

By virtue of the characteristics of the carbon/carbon composite material, the surgical instrument of the present invention enables heat generated by the occurrence of a spark discharge of the high-frequency current to be easily diffused, thus substantially eliminating the possibility of adhesion of carbonized body tissue proteins and fats which may be produced by the arc discharge or Joule heat attendant on the electrotomy or electrocoagulation, thereby to ensure continuous incising or coagulating technique.

BRIEF DESCRIPTION OF THE DRAWINGS

FIG. 1 is a view showing an example in which the concept of the present invention is applied to an electric knife; and FIG. 2 is a view showing an example in which the concept of the present invention is applied to a bipolar styptic forceps.

DESCRIPTION OF THE PREFERRED EMBODIMENTS

The present invention will now be described below by way of a non-limitative example thereof with reference to the accompanying drawings.

Referring first to FIG. 1, it exemplarily illustrates a surgical instrument according to the present invention which takes the form of a unipolar electric knife. The unipolar electric knife is generally designated at 1 and comprises an electric knife body 2 formed of a carbon/carbon composite material, and an insulating tube 3 with which the electric knife body 2 is sheathed.

The electric knife body 2 includes a knife tip electrode 4 formed on its distal end, and a holder portion 5 provided on its proximal end. The holder portion 5 of the unipolar electric knife 1 is intended to connect to a socket of a unipolar knife holder not shown, which is in turn connected to an electric operating apparatus not shown.

The electric knife body 2 is formed of a carbon/carbon composite obtained by calcining carbon filaments oriented in a single direction, each carbon filament having a diameter of 7 microns ($\mu$m) and impregnated with a phenolic resin. The knife tip electrode 4 is formed by machining the distal end of the electric knife body 2 into the shape of a blade. Upon the formation of the carbon/carbon composite, it is preferable that the distal ends of the carbon filaments be chamfered, since if the end faces of the carbon filaments are exposed on the surface of the knife tip electrode 4, the exposed parts will be liable to undergo adhesion of carbides of proteins and fats of living body tissue.

The carbon/carbon composite is a carbon/carbon composite material known in the art. The carbon/carbon composite is generally made of carbon fibers as a reinforcing material and a carbon matrix. It has a high resistance to heat, a high strength, elasticity, a high resistance to abrasion, and affinity to living body. The carbon matrix is made from carbon produced by thermal cracking of hydrocarbons, petroleum pitch, coal pitch or resins such as phenol resins. The carbon/carbon composite can be produced by either one of a carbonization method, a hot press method, a pressure impregnation and carbonization method and a combination of the above methods.

Tables 1 and 2 illustrate results of comparisons of the unipolar electric knife of the present invention and the conventional stainless steel electric knife and the Teflon-coated stainless electric knife.

Table 1 represents variations in outputs and states of knife tip at the time of performing electrotomy or electrocoagulation using pieces of ham as a sample.

TABLE 1

ELECTRIC KNIFE TIP EVALUATION FOR DIFFERENT MATERIALS

| | Stainless Steel | Teflon-Coated | Carbon/Carbon Composite |
|---|---|---|---|
| Minimum Discharge Start Output at First Spray Coagulation | 2 W | 10 W | 4 W |
| Spray Coagulation Mode Output after Several-times Use | 2 W | 5 W | 4 W |
| Visual Knife Tip Variation Level after Discharge Start | Substantially no variation | Black micro-spots appear on edge of knife. | Substantially no variation |
| Visual Knife Tip Variation after Several-ten-times Discharge (30 W) | Edge of knife blackened with adhesion of carbides. | Edge of knife blackened without carbides. | Fat film adhered to knife tip surface. |
| Visual Knife Tip Variation after Continuous Discharge (100 W) | Carbide adhesion level increased. | Slight carbide adhesion observed. | Slight carbide adhesion observed. |
| Electric Resistance after/before Use (Check by Tester) | conducting → conducting | insulating → conducting | conducting → conducting |

Table 2 represents carbide adhesion levels using pieces of ham as a sample.

TABLE 2

COMPARISON OF CARBIDE ADHESION LEVELS FOR DIFFERENT KNIFE TIP MATERIALS

| | Stainless Steel | Teflon-Coated | Carbon/Carbon Composite |
|---|---|---|---|
| Immediately After Using Knife | normal | very low | very low |
| When Heating Knife Tip | high | low | low |
| Carbide Removal | difficult | easy | easy |
| Means for Removal | exclusive cleaner | gauze wiping | gauze wiping |

These measurement results reveal that the unipolar electric knife of the present invention can fully perform its desired function after regenerative use or a number of times of use, since it has a less tendency for carbides to adhere to its knife tip and hence it does not need the knife tip cleaner which would otherwise give rise to a deformation of the knife tip due to abrasion.

It has been found that as the temperature of the knife tip is raised, the advantage of use of the carbon/carbon composite will become conspicuous over the stainless steel and the Teflon-coated stainless steel.

Referring now to FIG. 2, it exemplarily illustrates the surgical instrument of the present invention applied to a bipolar styptic forceps. The bipolar styptic forceps 10 comprises a pair of blades 11a and 11b which are joined together by means of an insulating piece not shown made of Bakelite or ceramics. In the same manner as the above-described electric knife body 2, the pair of blades 11a and 11b are formed of a carbon/carbon composite obtained by calcining carbon filaments oriented in a single direction, each carbon filament having a diameter of 7 microns ($\mu$m) and impregnated with a phenolic resin.

The reinforcing fibers of the carbon/carbon composite may be a plurality of carbon filaments intertwined or interweaved with one another instead of the unidirectionally oriented carbon filaments.

However, it has been found that the use of unidirectionally oriented carbon filaments is most desirable. Further, it has been found that as the compactness, bending strength and bending modulus of elasticity of the carbon/carbon composite increase, the adhesion of carbides will decrease. A comparison test was conducted using three kinds of carbon/carbon composites, which were:

1. AC100 (Produced and sold by TOHO RAYON KABUSHIKI KAISHA, Japan)

A carbon/carbon composite including short carbon filaments having a diameter of 7 $\mu$m and a length from 5 to 15 mm, which carbon fibers have been compacted with a phenolic resin and sintered. This composite has a low compactness, a bending strength from 8 to 15 Kgf/mm$^2$ and bending moudlus of elasticity of 3,000 to 5,000 Kg/mm$^2$.

2. AC250 (Produced and sold by TOHO RAYON)

A carbon/carbon composite including spun carbon filament yarn having a diameter of 7 $\mu$m, which carbon yarns have been compacted with a phenolic resin and sintered. This composite has a medium compactness, a bending strength from 30 to 35 Kgf/mm$^2$ and a bending modulus of elasticity of 8,000 to 10,000 Kg/mm$^2$.

3. AC400 (Produced and sold by TOHO RAYON)

A carbon/carbon composite including long, high-strength, unidirectionally-oriented carbon filament yarns having a diameter of 7 μm, which carbon filament yarns have been compacted with a phenolic resin and sintered. This composite has a high compactness, a bending strength of 40 to 45 Kgf/mm² and a bending modulus of elasticity of 25,000 to 30,000 Kgf/mm2.

Table 3 below shows results of comparison of performances of electric knives formed of AC100, AC250 and AC400.

TABLE 3

COMPARISON OF DIFERENT Carbon/Carbon COMPOSITES

|  | Compactness | Cutting Quality | Prevention of Carbides Adhesion |
| --- | --- | --- | --- |
| AC100 | low | good | good |
| AC250 | medium | good | very good |
| AC400 | high | good | superior |

After the use of the knives for about 30 seconds, any carbide adhesion was recognized for AC250 and AC400 on the surfaces but a film of oil was found on the surfaces to such a degree as to be easily wiped off with gauze. After a long use of the knives, however, a very small amount of carbides was recognized on the surfaces when the temperature of the knife tip is high. It was found that when the compactness is not sufficient a small amount of carbide adhesion tends to occur, probably for the reason that the surface roughness of the knife surface after the machining is relatively large so that voids exist between carbon fibers, tending to allow carbides to adhere. The reason why a very small amount of carbides was adherred for AC400 after a long use at high temeprature appears to be that the level of surface free energy increased due to the high temperature.

As was mentioned above, low compactness of the carbon/carbon composite used results in increase in surface roughness which leads to adhesion of carbides. For this reason and for increasing the strength, compactness of the carbon/carbon composite must be made high. This can be performed by carrying out a step of impregnating a thermosetting resin or a petroleum or coal pitch into a carbon/carbon composite after the composite is shaped, and/or by carrying out a step of recarbonization According to the present invention as described above, the characteristics of the carbon/carbon composite material enables heat generated by the occurrence of a spark discharge of high-frequency current to be easily diffused, thus substantially eliminating the possibility of adhesion of carbonized body tissue proteins and fats which may be produced by the arc discharge or Joule heat attendant on the electrotomy or electrocoagulation, thereby to ensure continuous incising or coagulating technique.

What is claimed is:

1. A surgical instrument comprising a body portion and a tip portion for contacting living body tissues, at least the tip portion being made of a carbon/carbon composite material.

2. A surgical instrument according to claim 1, wherein said tip portion is a tip electrode.

3. A surgical instrument according to claim 1, wherein said carbon/carbon composite material includes reinforcing carbon filament fibers oriented unidirectionally.

4. A surgical instrument according to claim 1, wherein said carbon/carbon composite material has a bending strength ranging from 8 to 45 Kgf/mm² and a bending modulus of elasticity ranging from 3,000 to 30,000 Kgf/mm².

5. A surgical instrument according to claim 1, wherein said carbon/carbon composite material has a bending strength ranging from 40 to 45 Kgf/mm² and a bending modulus of elasticity ranging from 25,000 to 30,000 Kgf/mm².

6. A surgical instrument according to claim 1, wherein said carbon/carbon composite material includes intertwined or interweaved reinforcing fibers.

7. An electric knife comprising a blade portion formed of a carbon/carbon composite material.

8. An electric knife according to claim 6, wherein said carbon/carbon material includes reinforcing carbon filament fibers oriented unidirectionally.

9. An electric knife according to claim 7, wherein said carbon/carbon composite material includes intertwined or interweaved reinforcing fibers.

10. An electric knife as claimed in claim 7, the electric knife further comprising:

(a) an electric knife body formed of a carbon/carbon composite material, the electric knife body having a distal end and a proximal end, the distal end being formed into the blade portion, the blade portion being a knife tip electrode;

(b) a holder portion on the proximal end of the electric knife body; and (c) an insulating portion sheathing the electric knife body between the proximal end and the distal end.

11. An electric knife as claimed in claim 10, wherein the carbon/carbon composite material has a bending strength ranging from 8 to 45 Kgf/mm² and a bending modulus of elasticity ranging from 3,000 to 30,000 Kgf/mm².

12. An electric knife as claimed in claim 10, wherein the carbon/carbon composite material has a bending strength ranging from 40 to 45 Kgf/mm² and a bending modulus of elasticity ranging from 25,000 to 30,000 Kgf/mm².

13. An electric knife as claimed in claim 7, wherein the carbon/carbon composite material has reinforcing carbon filament fibers oriented unidirectionally.

14. An electric knife as claimed in claim 7 wherein said carbon/carbon material includes intertwined or interweaved reinforcing fibers.

15. A surgical instrument as claimed in claim 1, wherein the carbon/carbon composite is impregnated with a thermosetting resin, a petroleum pitch, or a coal pitch.

16. A surgical instrument as claimed in claim 1, wherein the carbon/carbon composite is recarbonized.

17. An electric knife as claimed in claim 7, wherein the carbon/carbon composite is impregnated with a thermosetting resin, a petroleum pitch or a coal pitch.

18. An electric knife as claimed in claim 7, wherein the carbon/carbon composite is recarbonized.

* * * * *